United States Patent [19]

Pinchuk et al.

[11] Patent Number: 5,376,117
[45] Date of Patent: Dec. 27, 1994

[54] BREAST PROSTHESES

[75] Inventors: Leonard Pinchuk; John B. Martin, Jr., both of Miami, Fla.; Anne A. Maurin, Bazancourt, France

[73] Assignee: Corvita Corporation, Miami, Fla.

[21] Appl. No.: 975,979

[22] Filed: Nov. 13, 1992

Related U.S. Application Data

[63] Continuation of Ser. No. 782,396, Oct. 25, 1991, abandoned.

[51] Int. Cl.$^5$ .............................................. A61F 2/12
[52] U.S. Cl. ........................................... 623/8; 623/11
[58] Field of Search ..................... 623/8, 7, 11, 12, 1, 623/66

[56] References Cited

U.S. PATENT DOCUMENTS

| | | |
|---|---|---|
| 2,411,660 | 11/1946 | Manning . |
| 2,543,499 | 2/1951 | Kausch . |
| 2,593,002 | 4/1952 | Bernhardt . |
| 2,886,877 | 5/1959 | Frickert et al. . |
| 3,196,464 | 7/1965 | McKee . |
| 3,366,975 | 2/1968 | Pangman . |
| 3,559,214 | 2/1971 | Pangman ............................. 623/8 |
| 3,663,968 | 5/1972 | Mohl et al. . |
| 3,681,787 | 8/1972 | Perras . |
| 3,683,424 | 8/1972 | Pangman . |
| 4,044,404 | 8/1977 | Martin et al. . |
| 4,100,627 | 7/1878 | Brill . |
| 4,157,085 | 6/1979 | Austad . |
| 4,172,298 | 10/1979 | Rechenberg . |
| 4,323,525 | 4/1982 | Bornat . |
| 4,332,634 | 6/1982 | Aperavich ............................. 623/8 |
| 4,404,296 | 9/1983 | Schäpel ............................. 623/8 |
| 4,455,691 | 6/1984 | Van Aken Redinger et al. .... 623/8 |
| 4,470,160 | 9/1984 | Cavon . |
| 4,475,972 | 10/1994 | Wong ............................. 623/1 |
| 4,517,326 | 5/1985 | Cordts et al. . |
| 4,592,755 | 6/1986 | Penton et al. ............................. 623/8 |
| 4,650,487 | 3/1987 | Chaglassian . |
| 4,662,357 | 5/1987 | Pierce et al. . |
| 4,676,795 | 6/1987 | Grundei . |
| 4,701,230 | 10/1987 | Loi . |
| 4,713,073 | 12/1987 | Reinmuller . |
| 4,731,081 | 3/1988 | Tiffany et al. . |
| 4,739,013 | 4/1988 | Pinchuk . |
| 4,740,208 | 4/1988 | Cavon . |
| 4,769,036 | 9/1988 | Modir . |
| 4,772,284 | 9/1988 | Jefferies et al. . |
| 4,772,285 | 9/1988 | Ksander et al. . |
| 4,773,909 | 9/1988 | Chaglassian . |
| 4,787,905 | 11/1988 | Loi . |
| 4,790,848 | 12/1988 | Cronin . |
| 4,810,749 | 3/1989 | Pinchuk . |
| 4,826,501 | 5/1989 | Grundei . |
| 4,851,009 | 7/1989 | Pinchuk . |
| 4,963,150 | 10/1990 | Brauman ............................. 623/8 |
| 4,974,464 | 1/1989 | Eberl et al. . |

FOREIGN PATENT DOCUMENTS 1068052 12/1979 Canada .

OTHER PUBLICATIONS

Brochure–American Society of Plastic and Reconstructive Surgeons, Inc. (1984) This brochure generally describes Augmentation Mammaplasty.

*Primary Examiner*—David Isabella
*Attorney, Agent, or Firm*—Lockwood, Alex, Fitzbiggon & Cummings

[57] ABSTRACT

Breast prostheses for subcutaneous implantation for breast augmentation. The prostheses include an outer shell having a smooth non-porous outer envelope and a non-woven porous outer layer affixed to the envelope. The outer layer is preferably manufactured by an electrostatic spinning process to deposit biocompatible polymeric fibers on the smooth outer envelope of the prosthesis to build up a porous surface which promotes tissue ingrowth therein. In a preferred embodiment, the biocompatible porous outer layer and the non-porous outer envelope are manufactured with a polyurethane polymer material. Most preferably, a polycarbonate urethane polymer is used to manufacture the outer layer. The outer envelope and the porous outer layer may be further treated with an acetoxy-terminated siloxane to render them more crack-resistant under in vivo use.

14 Claims, 2 Drawing Sheets

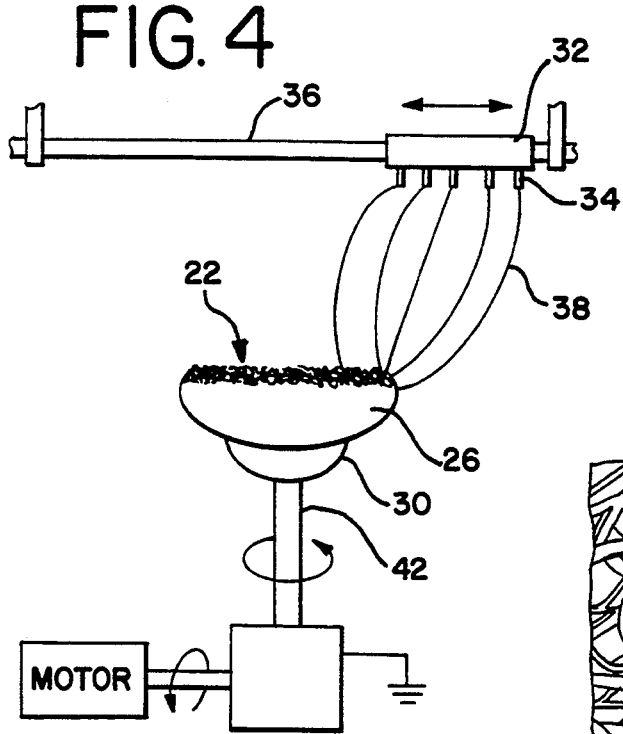
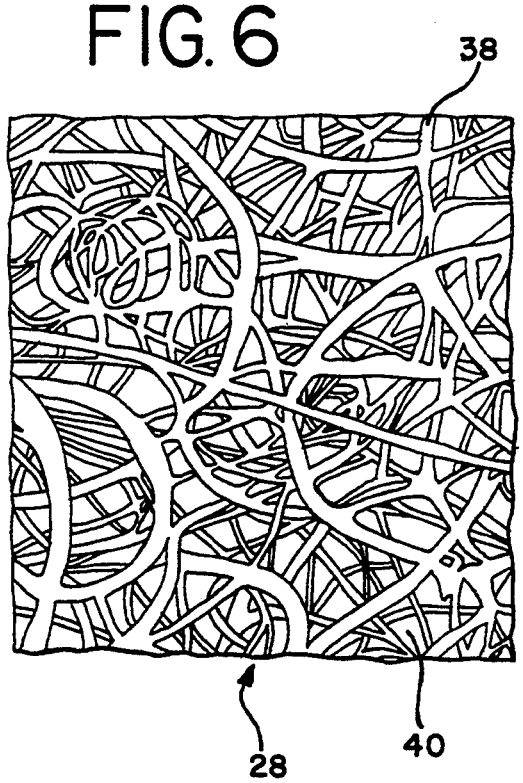
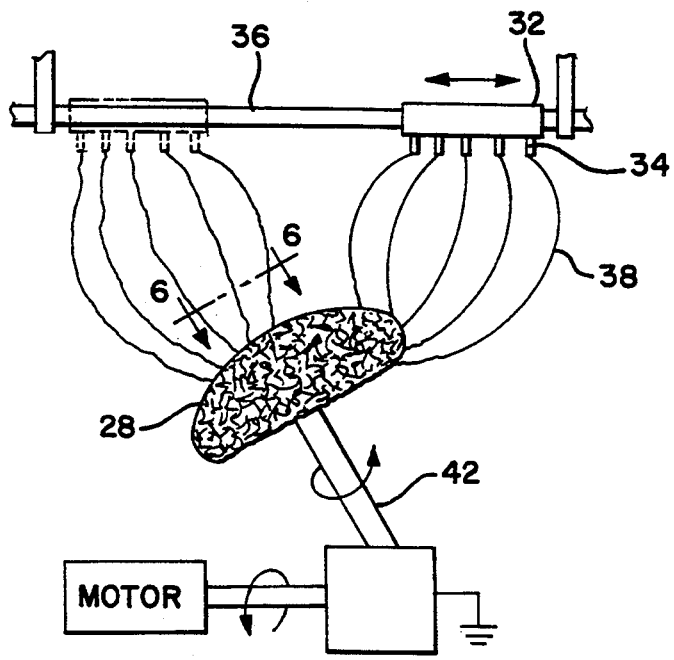

BREAST PROSTHESES

This application is a continuation of application Ser. No. 07/782,396, filed Oct. 25, 1991 now abandoned.

BACKGROUND AND BRIEF DESCRIPTION

This invention generally relates to breast prostheses and methods for manufacturing breast prostheses. More specifically, this invention relates to breast prostheses having a biocompatible outer shell which is stronger than more conventional designs. The present invention encompasses implants and the like wherein the outer shell includes a non-woven spun surface bonded to a non-porous outer envelope. The porous surface of the spun polyurethane promotes tissue ingrowth and may be further treated with a silicone rubber material to render it more crack resistant under in vivo conditions.

The typical breast prosthesis includes a silicone outer shell filled with a silicone based gel. The development and use of such implants generally began with the surgical injection of silicone gel under the skin to fill out wrinkles and to enlarge the breast. Due to the extensive migration of the silicone gel after injection, a sack or shell, typically made of silicone rubber, was adopted for use in such implants to enclose the gel and to prevent migration after implantation. Such a design which includes a silicone rubber outer shell is typical of modern breast implants. Such implants present several problems due to the nature of their construction and the materials selected therefor.

The silicone gel which is often used as a filler material within the silicone outer shell of the conventional prosthesis typically contains unreacted silicone oils. Such oils have been known to permeate through the silicone shell of the prosthesis and to find their way into the lymph nodes of the body, thereby presenting a potential cancer risk to the patient. Furthermore, the outer silicone rubber shell is inherently weak and cases have been documented wherein these outer shells have ruptured following implantation in the body. Consequently, an outer shell having a tensile strength higher than that of silicone rubber would be desirable.

The smooth wall of the typical silicone rubber outer shells of conventional breast implants are also believed responsible, at least in part, for contracture and migration of the prosthesis after implantation in a patient. Such a condition, commonly referred to as capsular contracture, results from the build up of hard scar tissue around the implant which can eventually cause contraction and some migration of the implant. This condition can become quite painful for the patient and can require additional surgery to break the capsule and perhaps remove the implant.

The present invention overcomes the aforementioned problems by providing a breast implant which is manufactured with an outer shell made of a material which is impermeable to the oils contained in the silicone gel filler material which is often used in such prostheses. The outer shell of the implant of the present invention is significantly stronger than prior art silicone rubber outer shells and is provided with a porous surface made of a non-woven polymer fiber which promotes tissue ingrowth.

In a preferred embodiment, the implant of the present invention is manufactured with an outer shell which includes a non-porous outer envelope and a porous outer layer on the outer surface of the envelope. The porous outer layer is made by spinning polymer fibers onto the smooth surface of the shell to build up a porous three dimensional structure which, after implantation, will promote tissue ingrowth. Most preferably, the outermost porous layer is manufactured with a polycarbonate urethane polymer which is highly resistant to in vivo cracking. The non-porous envelope may also be manufactured from a polycarbonate urethane polymer. When the aforementioned porous layer is manufactured from polyurethane materials other than polycarbonate urethane polymers, or from other polymers generally, in vivo cracking may be a problem which can be avoided by treating the fibers of the porous layer with a silicone-rubber material to render the fibers more crack resistant. A similar treatment of the non-porous outer envelope can be accomplished. The pores within the outer layer can be filled with an appropriate gel containing elutable drugs such as antimicrobials or antibiotics which may be bound to protamine to reduce the incidence of infection following implantation. Other useful drugs may be used such as steroids, heparin, corticoids, chemotherapy drugs, and the like.

In a preferred method for manufacturing the implant of the present invention, the shell is made on a polished and shaped mandril by dip-coating or pour-coating with an appropriate elastomer such as polyurethane or silicone rubber in a solvent, for example. The elastomer is cured or dried to form the non-porous outer envelope of the outer shell. Alternatively, the non-porous outer envelope of the outer shell can be made by rotational casting of the reactants of a polyurethane or a silicone rubber or by melting fine powders of a polyurethane.

While still on the mandril the envelope is placed on an electrically grounded rotating cup and rotated. A spinnerette is positioned over the rotating shell and is charged to a desired voltage. Fibers are extruded from the spinnerette and attracted to the grounded prosthesis under controlled temperature and humidity conditions to thereby provide a porous three dimensional outer layer which is bonded to and surrounds the non-porous outer envelope. Alternatively, the porous three dimensional outer layer can be made separately by electrostatically spinning polyurethane fibers onto a polished metal mandril and then removing the resulting structure from the mandril and placing it over the non-porous shell. The porous layer can be affixed to the outer shell of the implant either by use of an appropriate adhesive or by treating the outer shell with an appropriate solvent to promote bonding between the fibers and the smooth outer envelope. The porous outer layer and non-porous shell may be further treated with a silicone-rubber material to render the fibers more resistant to biodegradation under in vivo conditions.

The material used to fill the implant of the present invention may include the aforementioned silicone gels as well as other suitable substances known by those skilled in the art.

Accordingly, it is an object of the present invention to provide an implantable breast prosthesis which includes an outer shell which includes a non-porous outer envelope and a porous outer layer.

It is another object of the present invention to provide the aforementioned breast prosthesis with a porous three dimensional outer layer to promote tissue ingrowth after implantation in a patient.

It is still another object of the present invention to provide a method for the manufacture of a breast prostheses which includes electrostatically spinning a polymer material to form a three dimensional porous structure which will promote tissue ingrowth after implantation in a patient.

These and other objects of the present invention will be further appreciated by those skilled in the art following a review of the remainder of the present disclosure including the detailed description of the preferred embodiment and the claims.

BRIEF DESCRIPTION OF THE DRAWINGS

FIG. 4 is a schematic representation of an apparatus for manufacturing the prosthesis of the present invention, illustrating the manner in which the porous outer layer structure is applied to the posterior side of the prosthesis;

FIG. 5 is a schematic representation of an apparatus for manufacturing the prosthesis of the present invention illustrating the manner in which the porous outer layer is applied to the anterior side of the prosthesis; and FIG. 6 is representation of a scanning electron micrograph of the porous outer layer, taken along the 6—6 line of FIG. 5.

DETAILED DESCRIPTION OF THE PREFERRED EMBODIMENTS

Figure 1:
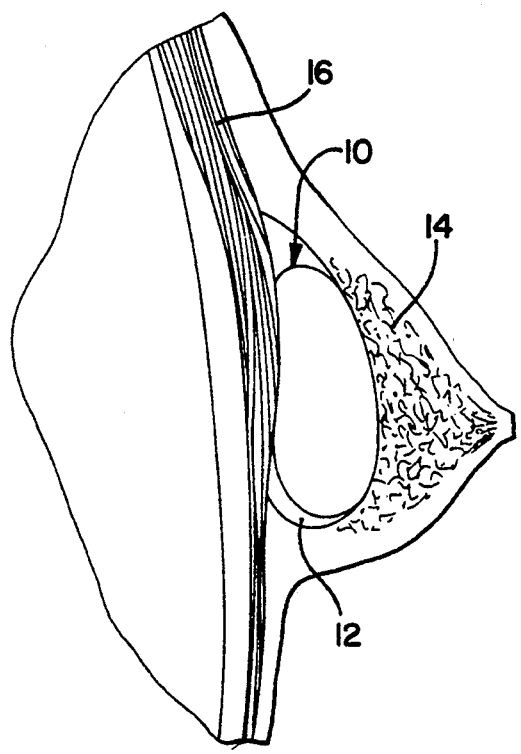
FIG. 1 is a side elevational view, in section of the prosthesis of the present invention after implantation under the breast tissue in a patient.

The present invention provides breast prostheses and a method for manufacturing such prostheses. Referring generally to FIGS. 1 through 6 herein, the prostheses and the method for manufacturing such prostheses are described in detail wherein like reference numerals indicate like elements.

Figure 2:
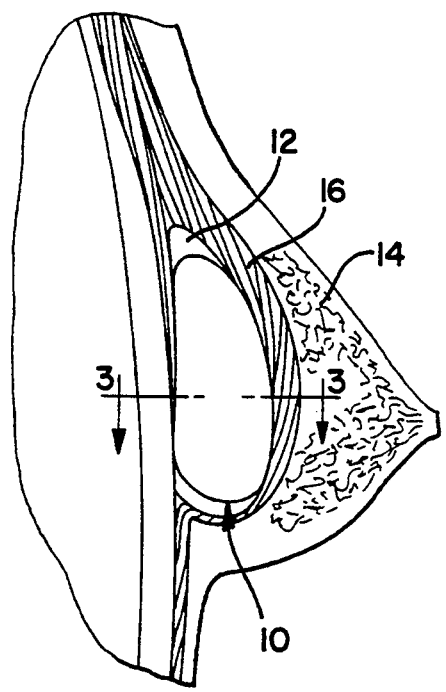
FIG. 2 is a side elevational view, in section, of the breast prosthesis of the present invention after implantation underneath the chest muscle of a patient.
Figure 3:
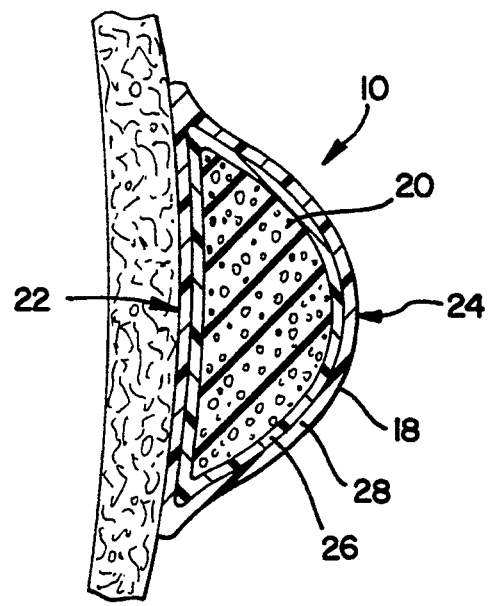
FIG. 3 is a view of the prosthesis depicted in FIG. 2, taken along the 3—3 line thereof.

Referring now to FIGS. 1 through 3, a breast prosthesis or implant 10, made in accordance with the principles of the present invention, is shown. As those skilled in the art will appreciate, the prosthesis 10 is implanted within a surgically created pocket, generally indicated by reference numeral 12. Such a pocket 12 may be created by the surgeon either directly under the breast tissue 14, as in FIG. 1, or underneath the chest wall muscle 16, as shown in FIG. 2.

As shown in FIG. 3, the implant 10 is manufactured with an outer shell 18 which can be filled with any of a variety of suitable materials such as saline solution, glycerin, silicone based gels, aqueous based gels such as gelatin, polyvinyl alcohol, polyvinylpyrrillidone, hyaluronic acid, polycarboxylic acid and the like to fill the implant 10 and form an inner soft core 20. The outer shell 18 and the inner core 20 are manufactured to be soft and pliable to thereby avoid imparting an unnecessary degree of firmness following surgery. Additionally, the implant 10 is manufactured with its outer shell 18 to include a posterior side 22 which is molded to seat against the chest wall of the patient to thereby avoid rotation or shifting of the prostheses 10 following implantation. The convex anterior side 24 preferably follows the natural contour of the breast to provide augmentation of the breast which is natural in contour and appearance.

The outer shell 18, in accordance with the principles of the present invention, is manufactured to include an outer envelope 26 and a porous non-woven fibrous coating 28 which overlies the outer envelope 26. Preferably, both the outer envelope 26 is manufactured from a polyurethane material and, most preferably, is manufactured from a crack-resistant polyurethane material such as a polycarbonate urethane polymer. Such polycarbonate urethane polymers, described in more detail below, generally provide a desired resistance to cracks and surface fissures under in vivo conditions. Other polyurethane materials may also be employed in the manufacture of the envelope 26 such as those described in U.S. Pat. Nos. 4,739,013 and 4,810,749. For example, polyurethane materials useful for the manufacture of the present invention can include, without limitation, polyether urethanes, polyester urethanes, polyurethane ureas, polyurethanes containing silicones and polyurethanes containing aliphatic soft segments, and the like.

Regarding the porous coating 28, polycarbonate urethane polymers are the most preferred material. However, those skilled in the art will also appreciate that the non-woven porous coating 28, may be made from a number of materials such as elastomeric silicone materials and various polymers. Siloxanes and fiber-forming polymers such as polyolefins, polyesters, nylons, teflon and the like are preferred. Most preferably, polycarbonate urethane polymer are employed. When such fiber-forming polymers are employed, an additional step of crack-guarding the polymer fibers is generally desired to adequately protect the coating 28 from cracking under in vivo conditions. Suitable crack guarding may be accomplished by treating the coating 28 with an acetoxy-terminated silicone rubber material, substantially in the manner disclosed in U.S. Pat. No. 4,851,009, the subject matter of which is incorporated by reference herein. Alternatively, the non-woven fibers of the porous coating 28 may be made exclusively from a suitable acetoxy-terminated silicone rubber material spun or deposited on the non-porous outer envelope 26 in the manner described herein.

In the preferred embodiment, the use of polyurethane materials renders the outer shell 18 of the prosthesis 10 both stronger and more biocompatible than the typical smooth-walled or textured outer shell of prior art prostheses made from silicone based materials. The use of polyurethane in the manufacture of the outer envelope 26 provides an implant which has an outer envelope 26 having a tensile strength greater than that of silicone rubber and where a polycarbonate urethane polymer is used, the outer shell is approximately three times stronger than that of silicone rubber. Accordingly, the risk of in vivo rupturing of the outer envelope 26 is substantially reduced by the use of the polyurethane outer envelope. A further advantage of using polyurethane polymers over silicone rubber is to prevent the migration of silicone oils or water vapor from the inner core 20 and through the outer envelope 26, a problem which is prevalent where silicone-based gels are used for the inner core material in conjunction with silicone rubber outer shells. It will be appreciated that the polyurethane shell can be placed within a silicone shell typically used for breast implants. In this concentric embodiment, the urethane inner shell may or may not be bonded to the external silicone shell. The aforementioned acetoxy-terminated silicone rubber material is also suitable for such silicone shells as well as the more conventional peroxide cured or platinum cured silicone. In this arrangement, the silicone shell will assist in rendering the urethane more resistant to in vivo degradation, as mentioned.

The silicone outer layer can be rendered porous by treating or manufacturing the outer layer in a manner generally known to those skilled in the art. Alternatively, a spun porous coating can be applied to the silicone outer layer, as discussed herein.

Referring now to the specific polycarbonate urethanes which are useful for inclusion in the prostheses of the present invention. These polymers are generally formed via a reaction involving an —OH or hydroxyl group of a polycarbonate macroglycol with an —NCO or isocyanate group of a diisocyanate. Another terminal —NCO or isocyanate group of the diisocyanate reactant reacts with a terminal hydroxyl (or amine) group of a chain extender. It will be appreciated by those skilled in the art that polyurethanes generally can also be synthesized with a macroglycol and an isocyanate without a chain-extender. However, commercially available urethanes typically include chain extenders.

With particular reference to the polycarbonate urethanes useful in the manufacture of prostheses in accordance with the present invention, polymerization typically will be carried out in the presence of a suitable solvent under appropriate reaction conditions suitable for the formation of fibers. However, the fibers may also be heat extruded and heat bonded to one another.

Generally, the polycarbonate component is characterized by repeating

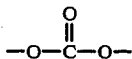

units, and a general formula for a polycarbonate macroglycol is as follows

HO—<[(—R—O—)$_y$—COO—]$_x$—(—R'O)$_y$>$_z$—H wherein x is from 2 to 35, y is 0, 1, 2 or 3, Z is 1 to 20, R and R' are cycloaliphatic, aromatic or aliphatic having from about 4 to about 40 carbon atoms or alkoxy having from about 2 to about 20 carbon atoms.

Examples of typical aromatic polycarbonate macroglycols include those derived from phosgene and bisphenol A or by ester exchange between bisphenol A and diphenyl carbonate such as (4,4'-dihydroxy-diphenyl-2,2'-propane) shown below, wherein n is between about 1 and about 12.

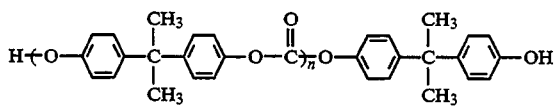

Typical aliphatic polycarbonates are formed by reacting cycloaliphatic or aliphatic diols with alkylene carbonates as shown by the general reaction below:

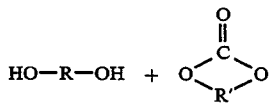

wherein R is cyclic or linear and has between about 1 and about 40 carbon atoms and wherein R' is linear and has between about 1 and about 4 carbon atoms.

Typical examples of aliphatic polycarbonate diols include the reaction products of 1,6-hexanediol with ethylene carbonate, 1,4-butanediol with propylene carbonate, 1,5-pentanediol with ethylene carbonate, cyclohexanedimethanol with ethylene carbonate and the like and mixtures of the above such as diethyleneglycol and cyclohexanedimethanol with ethylene carbonate.

When desired, polycarbonates such as these can be copolymerized with components such as hindered polyesters, for example phthalic acid, in order to form carbonate/ester copolymer macroglycols. Copolymers formed in this manner can be entirely aliphatic, entirely aromatic, or mixed aliphatic and aromatic. The polycarbonate macroglycols typically have a molecular weight of between about 200 and about 4000 Daltons.

Diisocyanate reactants according to this invention have the general structure OCN—R'—NCO, wherein R' is a hydrocarbon that may include aromatic or non-aromatic structures, including aliphatic and cycloaliphatic structures. Exemplary isocyanates include the preferred methylene diisocyanate (MDI), or 4,4-methylene bisphenyl diisocyanate, or 4,4'-diphenylmethane diisocyanate and hydrogenated methylene diisocyanate (HMDI). Other exemplary isocyanates include hexamethylene diisocyanate and the toluene diisocyanates such as 2,4-toluene diisocyanate and 2,6-toluene diisocyanate, 4,4'-toluidine diisocyanate, m-phenylene diisocyanate, 1,10-decamethylene diisocyanate, 1,4-cyclohexylene diisocyanate, 4,4'methylene bis (cyclohexylisocyanate), 1,4'-isophorone diisocyanate, 3,3'-dimethyl-4,4'-diphenylmethane diisocyanate, 1,5-tetrahydronaphthalene diisocyanate, and mixtures of such diisocyanates. Also included among the isocyanates applicable to this invention are specialty isocyanates containing sulfonated groups for improved hemocompatibility and the like.

Suitable chain extenders included in the polymerization of the polycarbonate urethanes should have a functionality that is equal to or greater than two. A preferred and well-recognized chain extender is 1,4-butanediol. Generally speaking, most diols or diamines are suitable, including the ethylenediols, 1,4-cyclohexanediol, propylenediols, ethylenediamine, 1,4-butanediamine, 1,4-cyclohexanediamine, methylene dianiline hetermolecules such as ethanolamine, reaction products of the aforementioned diisocyanates with water, combination of the above, additional macroglycols and the like.

The polycarbonate urethane polymers should be substantially devoid of any significant ether linkages (i.e., when y is 0, 1 or 2 as represented in the general formula hereinabove for a polycarbonate macroglycol), and it is believed that ether linkages should not be present at levels in excess of impurity or side reaction concentrations. While not wishing to be bound by any specific theory, it is presently believed that ether linkages account for much of the degradation that is generally experienced by polymers because oxidizing agents that are typically encountered in vivo, or otherwise, attack the ether linkage. Oxidation is experienced, and live cells probably catalyze degradation of these other polymers.

Because minimal quantities of ether linkages are unavoidable in the polycarbonate producing reaction, and because these ether linkages are suspect in the biodegradation of polyurethanes, the quantity of macroglycol should be minimized to thereby reduce the number of ether linkages in the polycarbonate urethane. In order to maintain the total number of equivalents of hydroxyl terminal groups approximately equal to the total number of equivalents of isocyanate terminal groups, minimizing the polycarbonate soft segment necessitates proportionally increasing the chain extender hard segment in the three component polyurethane system. Therefore, the ratio of equivalents of chain extender to macroglycol should be as high as possible. A consequence of increasing this ratio (i.e., increasing the amount of chain extender with respect to macroglycol) is an increase in hardness of the polyurethane. Typically, polycarbonate urethanes of hardnesses, measured on the Shore scale, less than 70 A show small amounts of biodegradation. Polycarbonate urethanes of Shore 75 A and greater show virtually no biodegradation.

The ratio of equivalents of chain extender to polycarbonate and the resultant hardness is a complex function that includes the chemical nature of the components of the urethane system and their relative proportions. However, in general, the hardness is a function of the molecular weight of both chain extender segment and polycarbonate segment and the ratio of equivalents thereof. Typically, for 4,4'-methylene bisphenyl diisocyanate (MDI) based systems, a 1,4-butanediol chain extender of molecular weight 90 and a polycarbonate urethane of molecular weight of approximately 2000 will require a ratio of equivalents of at least about 1.5 to 1 and no greater than about 12 to 1 to provide non-biodegrading polymers. Preferably, the ratio should be at least about 2 to 1 and less than about 6 to 1. For a similar system using a polycarbonate glycol segment of molecular weight of about 1000, the preferred ratio should be at least about 1 to 1 and no greater than about 3 to 1. A polycarbonate glycol having a molecular weight of about 500 would require a ratio in the range of about 1:2 to about 1.5:1.

The lower range of the preferred ratio of chain extender to macroglycol typically yields polyurethanes of Shore 80 A hardness. The upper range of ratios typically yields polycarbonate urethanes on the order of Shore 75 D. The preferred elastomeric and biostable polycarbonate urethanes for most medical devices would have a Shore hardness of approximately 85 A.

Generally speaking, it is desirable to control somewhat the cross-linking that occurs during polymerization of the polycarbonate urethane polymer. A polymerized molecular weight of between about 80,000 and about 200,000 Daltons, for example on the order of about 120,000 Daltons (such molecular weights being determined by measurement according to the polystyrene standard), is desired so that the resultant polymer will have a viscosity at a solids content of 43% of between about 900,000 and about 1,800,000 centipoise, typically on the order of about 1,000,000 centipoise. Cross-linking can be controlled by avoiding an isocyanate-rich situation. Of course, the general relationships between the isocyanate groups and the total hydroxyl (and/or amine) groups of the reactants should be on the order of approximately 1 to 1. Cross-linking can be controlled by controlling the reaction temperatures and shading the molar ratios in a direction to be certain that the reactant charge is not overly isocyanate-rich; alternatively a termination reactant such as ethanol can be included in order to block excess isocyanate groups which could result in cross-linking which is greater than desired.

Concerning the preparation of the polycarbonate urethane polymers, they can be reacted in a single-stage reactant charge, or they can be reacted in multiple stages, preferably in two stages, with or without a catalyst and heat. Other components such as antioxidants, extrusion agents and the like can be included, although typically there would be a tendency and preference to exclude such additional components when a medical-grade polymer is being prepared.

Additionally, the polycarbonate urethane polymers can be polymerized in suitable solvents, typically polar organic solvents in order to ensure a complete and homogeneous reaction. Solvents include dimethylacetamide, dimethylformamide, dimethylsulfoxide toluene, xylene, m-pyrrol, tetrahydrofuran, cyclohexanone, 2-pyrrolidone, and the like, or combinations thereof.

Regarding a method for manufacturing the prostheses 10, a shell is preferably made on a polished breast implant mold which is substantially semi-spherical in shape and is free of bumps, scratches, cracks and other surface irregularities, by pour-coating(or dip-coating) the mold with an appropriate elastomer solution such as a polyurethane, for example, until a desired thickness for the envelope is obtained. Where the outer shell is to be made with a polycarbonate urethane, the polymer concentration in solution should be between about 10 and about 25% by weight. Depending upon the concentration of the polymer solution used in the pour- or dip-coating step, more than one application of the polymer solution to the mold may be necessary to obtain the desired thickness for the outer shell 26.

It is important to evenly distribute the polyurethane solution on the surface of the mold before solvent evaporation is complete. An even distribution of the polymer solution may be accomplished by maintaining the shaft 42 and the mold for the outer shell 26 in a horizontal position during application of the polymer solution to the mold. Moreover, it may be preferable to apply an excess of polymer solution to the mold and drain off the excess at a low rotational speed for the mold. Where polycarbonate urethane polymer is being applied to the mold, the rotational speed for the mold will vary between about 0.5 rpm and about 2 rpm. It will be appreciated that the actual speed of rotation will vary depending upon the concentration of solution with a slower speed of rotation required for polymer solutions of high concentration.

The pour or dip-coating procedure should be carried out in a controlled environment. The vapors of many solvents for polymer solutions can be toxic thereby requiring the use of glove boxes or similar enclosures to confine these vapors and simultaneously provide adequate humidity control. Preferably, the outer shell 26 will be manufactured in such a closed environment in a dry atmosphere produced by a positive flow of either nitrogen or dry air which has been circulated through a tube of a suitable desiccant such as calcium sulfate. A filter may be employed to screen out any particles of the desiccant which may be carried by the flow of air or nitrogen. A 5 micrometer filter has been found suitable for such a purpose. Vapors produced during solvent evaporation in the glove box may be collected by a charcoal filter placed at the exit of the air circuit. It is recommended that the humidity within the glove box should be maintained below 30%, especially where polycarbonate urethanes are being used in the formation of the outer shell 26.

When the polymer solution has been applied to the mold, the solvent should be allowed to evaporate while the mold rotates at the same speed which allowed for an even distribution of the polymer. Mold rotation should be continued until solvent evaporation is complete. The time required to dry each coat depends upon the thickness of the polymer film applied to the mold, the concentration of the polymer solution used and the ease in which the solvent evaporates at a given temperature within the manufacturing environment. An additional coat of polymer can be applied once the film on the mold has been dried to a point where it is neither tacky nor soft. Generally, four or five hours of drying time is required between applications of additional polymer coats. Once the final coat has been dried, complete solvent evaporation is achieved by curing the polymer of the outer shell. For polycarbonate urethane polymer shells, a temperature of about 110° C. applied for a minimum of six hours is generally sufficient to achieve curing of the shell.

Alternatively, the shell can be manufactured by a rotational casting method wherein the polycarbonate urethane reactants are polymerized within a two-piece mold cavity. Such a casting is accomplished by charging the mold cavity with isocyanate, macroglycol, chain extender and catalyst. The mold is rotated in three dimensions and heated to about 80° C. In this manner, the inside of the cavity will be coated while the urethane polymerizes to produce a shell having no holes to patch. Lastly, the shell can be manufactured by rotational casting of a finely ground powder of the reacted polyurethane in the presence of heat.

A fiber spinning process, commonly referred to as "electrostatic spinning", is used to produce the outer layer 28 of the prostheses 10. The electrostatic spinning process has been generally described in U.S. Pat. No. 4,475,972, the subject matter of which is incorporated by reference herein. Generally, the principle behind electrostatic spinning is to electrostatically charge polymer fibers and accelerate the charged fibers in a static electric field for deposition of the fibers on an electrically grounded surface by producing a potential difference between the source of the fibers (a spinnerette) and a mandril, mold or other suitable surface.

With particular reference now to the manufacture of the outer layer 28 of the present invention, the envelope 26, while still on the mold, is placed on a rotating cup 30 as shown in FIG. 4, for example. A spinnerette 32 containing a plurality of nozzles 34 is positioned above the shell 26. The spinnerette is affixed along the axis 36 so that the spinnerette can be selectively positioned along the length of the axis. The spinnerette is charged to a voltage of between about 5,000 and about 20,000 volts. Under force of a positive flow source such as a pump (not shown), fibers 38 are extruded from a solution of a suitable elastomer such as an acetoxy-terminated siloxane or a polyurethane polymer, for example, through the nozzles 34 in a manner that is known to those skilled in the art. The charge differential between the spinnerette 32 and the electrically grounded mold and envelope 26 causes the fibers 38 to be attracted to the envelope 26. By rotation of the mold and the envelope 26, the fibers 38 are laid down upon the surface of the envelope to form a three dimensional porous structure of elastomer which forms the non-woven porous coating 28.

As shown in FIG. 6, scanning electron microscopy reveals the manner in which the fibers 38 form a randomly oriented non-woven structure which is replete with pores 40. The presence of such pores promotes tissue ingrowth therein which will aid in the prevention of contraction and/or migration of the implant, such as that which occurs from the formation of an excessive amount of scar tissue.

In forming the coating 28, the prosthesis 10 preferably is prepared in at least two stages by coating first the posterior side 22 of the implant 10, as shown in FIG. 4. Once the three dimensional fiber structure is built up on the posterior side, the prosthesis is turned over and placed on a short mandril and rotated to spin-coat the convex anterior side 24 of the implant, as shown in FIG. 5. As in the pour-coating step described above. Both temperature and humidity are critical factors in the spin coating of the prostheses and must be controlled.

In the spin-coating of the anterior side 24, the rotating axis 42 is preferably adjustable so that the axis of symmetry which is co-extensive with the axis 42 can be set at an oblique angle, substantially as shown in FIG. 5. In this manner, the spinnerette 32 can be shuttled along the axis 36 so that, in one position, the spinnerette is positioned substantially over the center of the outer envelope 26 and, in a second position, the spinnerette is positioned substantially over the peripheral edge of the envelope 26. By shuttling the spinnerette between the aforementioned two positions and while simultaneously rotating the mandril along the axis 42, a more uniform porous coat 28 is formed.

It will be appreciated that the non-woven porous coating 28 can be formed by spinning the fibers 38 directly on a polished mandril. The spun coating is then cured and removed from the mandril and subsequently fitted around the urethane envelope. The coating 28 may or may not be bonded to the urethane envelope and the envelope may be silicone coated or not, as desired.

To facilitate bonding, when desired, the non-porous outer envelope 26 is preferably treated with a suitable adhesive or a solvent prior to application of the elastomer fibers 38 or coating 28. An envelope 26 made of polyurethane, for example, can be treated with a solvent such as dimethylacetamide, tetrahydrofuran or mixtures thereof, to facilitate adherence of the first layer of fibers 38 or coating 28 to the envelope 26. An envelope 26 of silicone rubber can be suitably treated with an adhesive such as that known under the trade name of Medical Adhesive A from Dow Corning.

Those skilled in the art will appreciate that electrostatic spinning can produce fibers of smaller diameter than would be produced in the absence of a potential difference between the spinnerette and the mold or mandril. The reduction in fiber diameter can cause rapid solvent evaporation from the fibers which could result in weak fiber-to-fiber bonding during the process. Accordingly, adjustments may be required to obtain desired fiber diameters wherein the fibers retain a sufficient amount of solution to remain tacky and to promote bonding between the fiber layers during electrostatic spinning. Adjustments to the potential difference, the distance between the spinnerette 32 and the mold as well as to the flow of polymer through the nozzles 34 can be accomplished to optimize manufacturing conditions to produce the desired fiber diameter. When the outer layer 28 is to be manufactured with polycarbonate urethanes, a satisfactory set of parameters would include a potential difference of about 15,000 volts, a mold to spinnerette distance of four to six inches and a polymer flow of approximately 0.015 milliliters per minute (for a spinnerette having 30 nozzles).

In those cases where the fibers 38 are made of materials other than a substantially pure silicone rubber material, for example, a crack-guarding step may be performed after the outer envelope 26 is completely fiber coated, to protect the porous coating and underlying envelope from cracking following implantation. Crack-guarding is accomplished by coating the fibers of the non-woven porous coating with an acetoxy-terminated silicone rubber, substantially in the manner disclosed in U.S. Pat. No. 4,851,009, the subject matter of which is incorporated by reference herein. In general, crack guarding is a desired step where the outer layer 28 is made of a polymer other than a polycarbonate urethane.

It should also be appreciated that a porous coating 28 can be prepared by other methods, known in the art. For example, other methods for producing a porous material suitable in forming the coating include the use of conventional foaming or blowing agents such as carbon dioxide, Freon and the like. Phase inversion techniques are also contemplated as are elution methods using sodium chloride or a hydrophilic polymer such as polyvinyl-pyrrilidone.

Once the outer envelope is fiber coated, and possibly crack-guarded, the shell is removed from the mandril and the hole from which the mandril was removed is patched with a circle of similarly spun materials in a manner that is known to those skilled in the art. The patch may be bonded to the shell with an appropriate adhesive or solvent and a fill valve may be incorporated in the patch at this point if so desired. The core material may be placed within the outer shell at this point or, if a fill-valve is incorporated in the structure, the core material may be added later, either prior to or during implantation in a patient. Known materials such as silicone gels, glycerin or saline may be used to fill the implant. Other materials such as carbonaceous aqueous gels can also be used such as gelatin, collagen, fibrinogen, fat tissue, chitin, hyaluronic acid, starch and albumin, for example. Synthetic hydrogels such as polyacrylamide, poly (2-hydroxyethyl methacrylate), polymethacrylic acid, polyvinyl alcohol, polyvinylpyrrilidone, and mixtures thereof may also be suitable.

The porous surface of the outer shell can be treated to contain elutable drugs by filling the interstices of the outer surface with a gelatin containing bound drugs or drug linkers such a protamine. Antimicrobials or antibiotics can be bound to the protamine to reduce infection, for example. Steroids, heparin, corticoids, chemotherapy drugs and the like can also be added to the outer surface prior to implantation.

While the preferred embodiments of the present invention have been discussed and described in detail above, those skilled in the art will appreciate that various changes and modifications to the described embodiments are possible and are contemplated as being within the scope of the present invention, as defined in the following claims.

We claim:

1. A mammary prosthesis for surgical implantation, comprising:
   an outer shell including a non-porous outer envelope made of a biocompatable polymeric material and a porous outer layer surrounding said non-porous envelope;
   said biocompatible polymeric material of said non-porous outer envelope being selected from the group consisting essentially of a polyurethane, a polycarbonate urethane, an elastomeric silicone material or a combination thereof, said outer envelope being resistant to in vivo cracking and to prevent leakage therethrough of any filler materials contained therein;
   said porous outer layer composed of extruded fibers of a polycarbonate urethane polymer material which is resistant to cracking under in vivo conditions, said fibers positioned on said outer layer in layers overlying and affixed to each other to form a non-woven surface having a network of pores conducive to tissue ingrowth thereinto, said polycarbonate urethane polymer material comprises the reaction product of a reactant charge, said reactant charge including a polycarbonate glycol reactant having terminal hydroxyl groups, a diisocyanate reactant having terminal isocyanate groups, and a chain extender reactant having terminal hydroxyl or amine groups, said reaction product having a hardness of at least about Shore 70 A and having a polymeric backbone having recurring groups selected from a group consisting of urethane groups, urea groups, carbonate groups and combinations thereof; and
   a soft filler material contained within said outer envelope.

2. A mammary prosthesis for surgical implantation, comprising:
   an outer shell including a non-porous outer envelope made of a biocompatable polymeric material and a porous outer layer surrounding said non-porous envelope;
   said biocompatible polymeric material of said non-porous outer envelope being selected from the group consisting essentially of a polyurethane a polycarbonate urethane, an elastomeric silicone material or a combination thereof, said outer envelope being resistant to in vivo cracking and to prevent leakage therethrough of any filler materials contained therein;
   wherein said polycarbonate urethane polymer of said non-porous outer envelope comprises the reaction product of a reactant charge, said reactant charge including a polycarbonate glycol reactant having terminal hydroxyl groups, a diisocyanate reactant having terminal isocyanate groups, and a chain extender reactant having terminal hydroxyl or amine groups, said reaction product having a hardness of at least about Shore 70 A and having a polymeric backbone having recurring groups selected from a group consisting of urethane groups, urea groups, carbonate groups and combinations thereof;
   said porous outer layer is composed of extruded fibers of a polycarbonate urethane polymer material which is resistant to cracking under in vivo conditions, said fibers positioned on said outer layer in layers overlying and affixed to each other to form a non-woven surface having a network of pores conducive to tissue ingrowth thereinto: and
   a soft filler material contained within said outer envelope.

3. The prosthesis of claim 1 wherein said filler material is selected from a group consisting essentially of silicone gels, saline, gelatin, collagen, chiten, starch, abumin, glycerin, hyaluronic acid and hydrogels of polyacrylamide, poly (2-hydroxyethyl methacrylate), polymethacrylic acid, polyvinyl alcohol, polyvinylpyrrolidone, and mixtures thereof.

4. The prosthesis of claim 1 wherein said porous outer layer includes a crack preventative material absorbed to and grafted on to said fibers so that there is bonding between said polycarbonate urethane polymer material and said crack preventative, said crack preventative being a siloxane including recurring

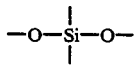

groups, said polycarbonate urethane polymer material having a surface tension greater than the predetermined surface tension of said crack preventative.

5. A mammary prosthesis for surgical implantation, comprising:

an outer shell including a non-porous outer envelope made of a biocompatible polymeric material and a porous outer layer surrounding said non-porous outer envelope, said outer envelope being made from a polycarbonate urethane material resistant to cracking under in vivo conditions when said prosthesis is implanted within a patient;

said porous layer being composed of extruded fibers selected from the group consisting essentially of a polycarbonate urethane polymer, a polyurethane polymer, an elastomeric silicone material or a combination thereof, said fibers being resistant to in vivo cracking when the prosthesis is implanted within a patient, said fibers positioned on said outer layer in layers overlying and affixed to each other to form a non-woven surface having a plurality of pores conducive to tissue ingrowth thereinto;

said polycarbonate urethane polymer comprising the reaction product of a reactant charge, said reactant charge including a polycarbonate glycol reactant having terminal hydroxyl groups, a diisocyanate reactant having terminal isocyanate groups, and a chain extender reactant having terminal hydroxyl or amine groups, said reaction product having a hardness of at least about Shore 70 A and having a polymeric backbone having recurring groups selected from a group consisting of urethane groups, urea groups, carbonate groups and combinations thereof; and a soft filler material contained in said outer envelope.

6. The prosthesis of claim 5 wherein said polycarbonate urethane polymer of said outer envelope comprises, the reaction product of a reactant charge, said reactant charge including a polycarbonate glycol reactant having terminal hydroxyl groups, a diisocyanate reactant having terminal isocyanate groups, and a chain extender reactant having terminal hydroxyl or amine groups, said reaction product having a hardness of at least about Shore 70 A and having a polymeric backbone having recurring groups selected from a group consisting of urethane groups, urea groups, carbonate groups and combinations thereof.

7. The prosthesis of claim 5 wherein said filler material is selected from a group consisting essentially of silicone gels, saline, gelatin, collagen, chiten, starch, abumin, glycerin, hyaluronic acid and hydrogels of polyacrylamide, poly (2-hydroxyethyl methacrylate), polymethacrylic acid, polyvinyl alcohol, polyvinylpyrrolidone, and mixtures thereof.

8. A mammary prosthesis for surgical implantation, comprising:

an outer shell including a non-porous polymeric shell and an elastomeric silicone based shell surrounding said polymeric shell; said outer shell preventing migration therethrough of any filler material contained therein and being resistant to cracking under in vivo use when the prosthesis is implanted in a patient, said outer shell being made from a polycarbonate urethane material;

said non-porous polymeric shell being selected from the group consisting essentially of a polyurethane material, a polycarbonate urethane material or a combination thereof and said polycarbonate urethane polymer comprises the reaction product of a reactant charge, said reactant charge including a polycarbonate glycol reactant having terminal hydroxyl groups, a diisocyanate reactant having terminal isocyanate groups, and a chain extender reactant having terminal hydroxyl or amine groups, said reaction product having a hardness of at least about Shore 70 A and having a polymeric backbone having recurring groups selected from a group consisting of urethane groups, urea groups, carbonate groups and combinations thereof;

a porous layer surrounding said silicone based shell, said porous layer being composed of extruded fibers of a biocompatible material, said fibers positioned on said silicone based shell in layers overlying and affixed to each other to form a non-woven surface having a plurality of pores conducive to tissue ingrowth thereinto; and a soft filler material contained within said outer shell.

9. The prosthesis of claim 8 wherein said elastomeric silicone based shell is composed of an elastomeric siloxane having recurring

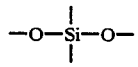

groups.

10. The prosthesis of claim 8 further comprising a porous layer surrounding said silicone based shell, said porous layer being composed of fibers of a polyurethane polymer, a polycarbonate urethane polymer, an elastomeric silicone based material or a combination thereof, said fibers overlying each other to form a non-woven porous surface which is conducive to tissue ingrowth;

said polycarbonate urethane polymer is the reaction product of a reactant charge, said reactant charge including a polycarbonate glycol reactant having terminal hydroxyl groups, a diisocyanate reactant having terminal isocyanate groups, and a chain extender reactant having terminal hydroxyl or amine groups, said reaction product having a hardness of at least about Shore 70 A and having a polymeric backbone having recurring groups selected from a group consisting of urethane groups, urea groups, carbonate groups and combinations thereof.

11. The prosthesis of claim 10 wherein said porous layer includes a crack preventative absorbed to and grafted on to said fibers so that there is bonding between said extruded biocompatible polymer material and said crack preventative, said crack preventative being an elastomeric silicone material having a predetermined surface tension, said crack preventative being a siloxane including recurring

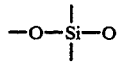

groups, said biocompatible polymeric material having a surface tension greater than the predetermined surface tension of said crack preventative; and said fibers of an extruded biocompatible polymer material consisting essentially of a polyurethane.

12. The prosthesis of claim 28 wherein said filler material is selected from a group consisting essentially of silicone gels, saline, gelatin, collagen, chiten, starch, abumin, and hydrogels of polyacrylamide, poly (2-hydroxyethyl methacrylate), polymethacrylic acid, polyvinyl alcohol, polyvinylpyrrolidone, and mixtures thereof.

13. A mammary prosthesis for surgical implantation, comprising:

an outer shell including a non-porous polymeric shell made from a polycarbonate urethane material and a silicone elastomer shell surrounding and affixed to said polymeric shell;

a porous layer affixed to said silicone elastomer, said porous layer composed of extruded fibers of a biocompatible material resistant to cracking under in vivo conditions, said fibers positioned on said silicone elastomer shell in layers, said fibers overlying and affixed to each other to form a non-woven surface having a plurality of pores conducive to tissue ingrowth thereinto; and a filler material contained within said outer shell;

said outer shell being resistant to cracking under in vivo conditions and preventing the migration therethrough of said filler material contained therein.

14. The prosthesis of claim 13 wherein said extruded fibers of said porous layer are made from materials selected from the group consisting essentially of silicone based elastomers, polyurethanes, polycarbonate urethanes and combinations thereof.

* * * * *

UNITED STATES PATENT AND TRADEMARK OFFICE
CERTIFICATE OF CORRECTION

PATENT NO. : 5,376,117
DATED : December 27, 1994
INVENTOR(S) : Leonard Pinchuk, John B. Martin and Anne B. Maurin It is certified that error appears in the above-indentified patent and that said Letters Patent is hereby corrected as shown below:

On the cover page, under "Inventors", line 2, replace "A." with --B.--; line 3, replace "Bazancourt" with --Songeons--; under References Cited, "U.S. PATENT DOCUMENTS", reference 4,100,627, replace "1878" with --1978--; reference 4,475,972, replace "1994" with --1984--; replace reference number "4,974,464" with --4,794,464--.

In the Abstract of the Disclosure, lines 16-17, "in vivo" should be underlined.

Col. 1, line 18, "in vivo" should be underlined.

Col. 2, lines 6-7, 12, and 53, "in vivo" should be underlined.

Col. 4, line 9, "in vivo" should be underlined; line 26, "polymer are" should read --polymers are--; lines 30, 51, and 68, "in vivo" should be underlined.

Col. 5, line 37, replace "Z" with --z--.

Col. 6, line 42, "hetermolecules" should read --heteromolecules--; line 56, "in vivo" should be underlined.

Col. 11, line 42, "such a" should read --such as--; line 66, "in vivo" should be in italics.

UNITED STATES PATENT AND TRADEMARK OFFICE
CERTIFICATE OF CORRECTION

PATENT NO. : 5,376,117

DATED : December 27, 1994

INVENTOR(S) : Leonard Pinchuk, John B. Martin and Anne B. Maurin

It is certified that error appears in the above-indentified patent and that said Letters Patent is hereby corrected as shown below:

```
Col. 12, line 3, "in vivo" should be in italics; line 30, "polyurethane
       a" should read --polyurethane, a--; lines 33 and 51, "in vivo"
       should be in italics.
Col. 13, lines 19 and 25-26, "in vivo" should be in italics.
Col. 14, line 2, "in vivo" should be in italics.
Col. 15, line 12, "28" should read --8--.
Col. 16, lines 5-6 and 12-13, "in vivo" should be in italics.
```

Signed and Sealed this

Twenty-first Day of May, 1996

Attest:

BRUCE LEHMAN

*Attesting Officer*   Commissioner of Patents and Trademarks